United States Patent [19]

Bonner et al.

[11] 4,153,416
[45] May 8, 1979

[54] PROCESS AND APPARATUS FOR PULSE LABELLING PROTEIN MATERIAL IN THE EDMAN DEGRADATION PROCESS

[76] Inventors: Alex G. Bonner, 23 Fairway Dr., West Newton, Mass. 02165; Marcus J. Horn, 1106 Boylston St., Newton Upper Falls, Mass. 02164

[21] Appl. No.: 803,689

[22] Filed: Jun. 6, 1977

[51] Int. Cl.$^2$ .................. G01N 1/18; C07C 103/52
[52] U.S. Cl. ................. 23/230 A; 23/230 R; 260/112.5 R; 422/67; 422/71.
[58] Field of Search ............ 23/253 R, 253 A, 252 R, 23/230 A, 230.3, 230.6, 230 R, 230 B; 260/112.5

[56] References Cited

U.S. PATENT DOCUMENTS

| | | | |
|---|---|---|---|
| 3,531,258 | 9/1970 | Merrifield et al. | 23/252 R |
| 3,557,077 | 1/1971 | Brunfeldt et al. | 23/253 A |
| 3,647,390 | 3/1972 | Kubodera et al. | 23/253 R |
| 3,725,010 | 4/1973 | Penhasi | 23/253 R |

Primary Examiner—R. E. Serwin

[57] ABSTRACT

A process and apparatus for pulse labelling protein material for high sensitivitiy sequence analysis of protein material by Edman degradation technique comprising an isolated, auxiliary unit for storing a radioactive coupling reagent together with tubes, valves and controls for interrupting the Edman process, for pumping a measure of radioactive coupling reagent into the reaction vessel, a timer for controlling duration of contact between the radioactive reagent, and the protein material to maximize the coupling reaction therebetween, and thereafter reactivating the Edman process to admit nonradioactive coupling reagent to the vessel and to drive the coupling reaction to completion.

5 Claims, 2 Drawing Figures

PROCESS AND APPARATUS FOR PULSE LABELLING PROTEIN MATERIAL IN THE EDMAN DEGRADATION PROCESS

BACKGROUND OF THE INVENTION

The field of the present invention is high sensitivity sequence analysis using radioactively labelled phenyl isothiocyanate (PITC) in the Edman degradation of peptides and proteins.

High sensitivity sequence analysis using radioactively labelled PITC has been demonstrated by a number of investigators. Bridgen, et. al., Nature, Vol. 261 (1976) 200; Howard, Nature, Vol. 261 (1976) 189; Silver and Hood, Proc. Nat. Acad, Sci. Vol. 73 (1976) 599; Bridgen, FEBS Letters Vol. 50 (1975) 159; Silver and Hood, Anal. Biochem. Vol. 67 (1975) 392; Jacobs, Niall, et. al., Fed. Proc. Vol. 32 (1973) 2445.

The principles of the Edman degradation technique for high sensitivity analysis of peptides and proteins are well-known. Briefly, the process can be described as follows. First, the protein or peptide is covalently bonded to an inert support, such as a polystyrene or glass support. While in a reaction column, this peptide or protein undergoes a coupling step, a labelling procedure using radioactive and then non-radioactive PITC. A buffer solution is pumped simultaneously with the radioactive and non-radioactive PITC, and preferably for a period of time thereafter to clean the lines. After this coupling step, the phenylthiocarbamyl peptide or protein is washed first with methanol and then with dichloroethane (DCE). The sample then undergoes a cleavage step by being treated with anhydrous trifluoroacetic acid (TFA). After the cleavage step, the protein or peptide derivatives in the reaction column are preferably washed with methanol. The resulting product after this cleavage step is an anilinothiazolinone (ATZ) amino acid derivative, which is usually unstable and normally requires a conversion step to a phenylthiohydantoin (PTH) amino acid derivative. These PTH derivatives are then identified by conventional means.

The use of $^{35}$S- or $^{14}$C- or $^{3}$H- labelled radioactive PITC provides labelled PTH amino acids that can be identified by two dimensional thin layer chromatography and autoradiography, or by isotope dilution and chromatography. While as little as 2 to 5 nanomoles of peptide or protein is sufficient for sequence determination of 15–20 residues, sequence determinations have been made on as little as picomolar quantities of protein and peptide using the above high sensitivity techniques.

The disadvantages of the prior art high sensitivity sequence determinations are numerous. First, with prior art techniques, the standard sequencer plumbing system had to be extensively modified whenever the operator wanted to introduce the radioactive PITC for labelling the protein material, a process step which is called "microsequencing" in the industry. ("Microsequencing" as used herein is intended to convey the concept of separate introduction of a radioactive reagent for labelling in the Edman degradation process. Typically, in the solid phase form in the prior art the radioactive PITC would be installed to replace the non-radioactive PITC. Then the non-radioactive PITC would be installed to replace the buffer reagent. Finally, the buffer reagent would be moved to replace the DCE reagent and the DCE reagent would be eliminated altogether. These numerous plumbing changes made the microsequencing set-up a semi-permanent situation. Interchangeability between the standard sequencer plumbing system and the microsequencing system was time consuming and hazardous to the operator because of the handling of radioactive material. Also the elimination of the DCE reagent results in lower yields for the overall sequence analysis of peptides and proteins.

SUMMARY OF THE PRESENT INVENTION

The labelling process and apparatus of the present invention overcomes the disadvantages of the prior art, and in addition provides useful flexibility. The present invention comprises an auxiliary system to provide complete and independent control for the delivery of radioactively labelled PITC. This auxiliary system for high sensitivity analysis is designed to be adapted to conventional Edman degradation sequencing systems. The present invention is an independent, modular add-on system. This isolated and independent design provides facile introduction of the radioactive reagent (PITC), which thus eliminates hazardous manipulations and change-over operations that are encountered in prior art systems.

The process and apparatus of the present invention comprises an independently programmed control unit and an isolated liquid system. The control unit comprises a programmable timer, an adjustable time delay means, and function switches. The liquid system comprises a valve, a pump, and a reagent bottle for containing the radioactive PITC.

In operation, the process and apparatus forms a part of an overall Edman degradation sequence system which is controlled by what is herein termed the main sequencer programmer. The present invention is useful in facilitating the coupling step of the degradation technique using a pulse label of radioactive PITC, thereby providing an economical consumption and safe use of the expensive and hazardous radioactive reagent.

The timer is programmed to provide automatic radioactive PITC pumping for a selected period of time. Also, the adjustable time delay means can then be set to allow the radioactive PITC to stand in the reaction column of the overall sequencer system. The time delay means allows the coupling reaction with radioactive PITC to be maximized. After this time delay, the coupling step is completed with non-radioactive PITC according to the remaining PITC delivery time of the main sequencer program. During this step the coupling step with non-radioactive PITC is brought to completion. The remainder of the Edman degradation technique can then be carried out according to the main sequencer program for that particular cycle. The timer and time delay means of the microsequencing system reset automatically at the end of the main PITC cycle, and are ready for the coupling step with radioactive PITC during the next cycle of degradation.

It is an objective of the present invention to provide a safe and efficient system for high sensitivity sequence analysis of as little as picomole and low nanomole amounts of proteins and peptides.

It is also an objective of the present invention to provide a flexible system for such high sensitivity analysis, wherein the microsequencing system is added onto a solid phase Edman sequencer system wherein the reaction columns of various sizes may be readily interchanged.

A further objective of the present invention is to provide a microsequencing system with fine time accuracy, permitting thereby precise and economical use of reagents.

Another objective of the present invention is to completely isolate the hazardous radioactive microsequencing system, while still permitting a user simple remote control to insert a pulse labelling procedure at any time. The hazardous handling of radioactive reagent is thereby minimized.

A further objective of the present invention is to permit an operator the flexibility to easily and readily perform manual experiments during any number of degradation cycles, wherein the amount of radioactive PITC delivered and duration of time delay can be readily altered if desired.

DETAILED DESCRIPTION OF THE PREFERRED EMBODIMENT

Figure 1:
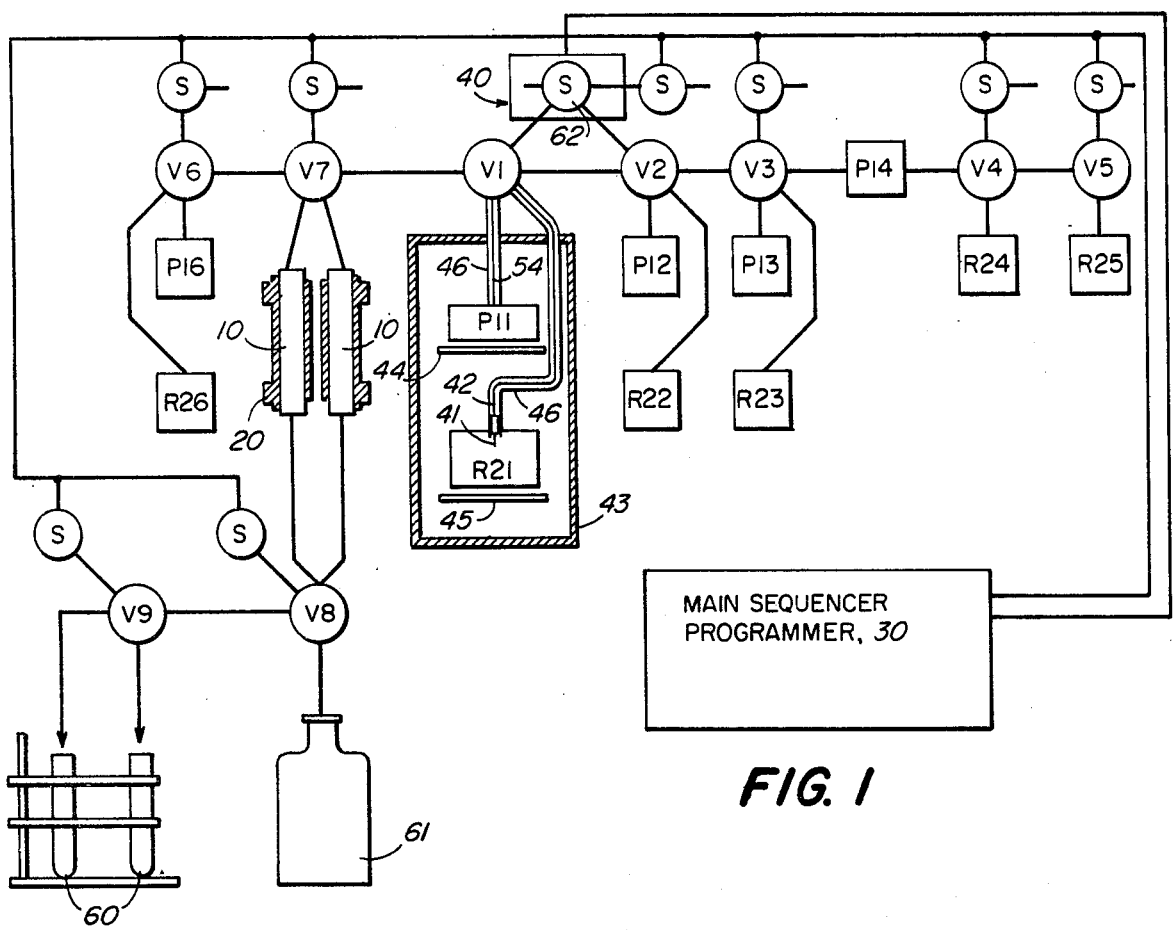
FIG. 1 is a schematic view of the system and apparatus of the present invention.

A preferred embodiment of the present invention is shown in the drawings. In reference thereto and first to FIG. 1, therein is shown the microsequencing system of the present invention as part of a complete solid phase Edman degradation sequencing system. As shown in FIG. 1, the microsequencing system is a modular add-on unit useful for quick, safe, and effective introduction of radioactive PITC into the degradation cycles of proteins and peptides, and wherein the radioactive reagent may be easily introduced during any cycle. Although the preferred embodiment concerns the auxiliary introduction of radioactive PITC into the main sequencing cycle, it is to be understood that the present invention is not limited to PITC in particular. The microsequencing system is useful for the separate introduction of any reagent which may be introduced during some but not necessarily all of the cycles, or any portions thereof, of the degradation process. Other microsequencing reagents, in addition to either radioactive or non-radioactive phenyl isothiocyanate, which can be successfully used with the microsequencing system of the present invention include allyl isothiocyanate, fluorescein isothiocyanate, 3-fluorophenyl isothiocyanate, 4-fluorophenyl isothiocyanate, methyl isothiocyanate, 1-naphthyl isothiocyanate, 2-naphthyl isothiocyanate, 4-(N,N-dimethylamino)-1-naphthyl isothiocyanate, p-phenylazophenyl isothiocyanate, and thioacetylthioglycolic acid, all of which may be either radioactive or non-radioactive, as well as other reagents obvious to those skilled in the art. Furthermore, it is to be understood that the term "microsequencing" does not necessarily limit the present invention to the analysis of small quantities of peptides or proteins.

The sequencing system of FIG. 1 shows the conventional system, or main system, for solid phase Edman degradation plus the microsequencing system of the present invention. The sample of protein or peptide to be analyzed is placed in a reaction column or columns, 10, which are surrounded by a heater or water bath 20. The microsequencing system then permits delivery of radioactive PITC which is an auxiliary step to the main non-radioactive PITC coupling step. The microsequencing system of the present invention comprises an independently programmed control unit 40 and an isolated liquid system. As shown in FIG. 1, the liquid system comprises an Aux. PITC valve 1, an Aux. PITC pump 11, and an Aux. PITC reagent bottle 21.

The Aux. PITC valve 1 is preferably an automatic slider valve, having fluid contact parts exclusively of Kel-F and Teflon, and outer body parts of Delrin or Tefzel. The Aux. PITC valve 1 of the preferred embodiment is Part No. 201-14 of the Altex Scientific Co. The present invention is not, however, to be construed as limited to this specific valve model. The slider valve is pneumatically activated by means of a 70 psi nitrogen system in the main sequencer. As part of a main sequencer system, it is contemplated that there will be a reservoir of nitrogen gas under a pressure of 70 psi, which will, upon signals from the main sequencer programmer 30, activate electrical solenoids (S) to release and restrict the gas pressure on the valves. Other valve systems suitable for the purposes disclosed herein and obvious to those skilled in the art may be used instead. A spring return actuator on the valve automatically returns the valve slider when nitrogen pressure is released. In practice, the main sequencer programmer 30 provides an automatic or manual electrical signal for PITC which actuates a solenoid valve to deliver 70 psi nitrogen. This nitrogen signal passes to a 4-way solenoid valve 62 located in the microsequencing control unit 40. The electrical signals from the microsequencing control unit 40 are used to control the 4-way solenoid valve 62 for pneumatic actuation of the slider valves 1, 2 for either radioactive or non-radioactive PITC.

The Aux. PITC pump 11 is preferably a bidirectional syringe pump, so that only glass and Teflon are in contact with the radioactive reagent PITC. The Aux. PITC pump 11 of the preferred embodiment is Model No. 1100 of the Harvard Apparatus Co. The present invention is not, however, to be construed as limited to this specific pump model. The pump 11 is supplied with a 2 ml syringe and interchangeable plug-in motor to provide constant speed for precise syringe pumping. The flow rate is fixed and cannot be accidentally altered. The pump 11 has a 2 rpm motor which provides a pumping rate of 0.13 ml per minute. Furthermore, low cost, interchangeable motors or alternate size syringes may be added to provide integrally variable flow rates of 0.01–0.50 ml per minute.

The Aux. PITC reagent bottle 21 is preferably a 30 ml disposable, septum topped vial for instant access and complete protection. Aluminum seals applied by a hand crimper are used for securing neoprene septa to the mouth of the vial. The Aux. PITC reagent bottles are filled and sealed at a safety work area. The Aux. PITC reagent bottle 21 is inserted into the liquid line of the main sequencer system by puncturing the septum with a syringe needle 41 which terminates the Teflon line 42 connecting the Aux. PITC pump 11 through Aux. PITC valve 1. The Aux. PITC pump 11 and reagent bottle 21 are located in a completely enclosed aluminum cabinet 43, where both the pump 11 and reagent bottle 21 have catch trays 44, 45 for safety.

All liquid lines connecting the Aux. PITC valve 1, pump 11, and reagent bottle 21 are Teflon tubing 42, and all connections are Teflon-to-Teflon or Teflon-to-glass with zero dead volume. Connections between the Aux. PITC valve 1, pump 11, and bottle 21 are made with narrow-bore Teflon tubing (0.023-inch i.d.). The lines 54, 42 from the Aux. PITC pump 11 and bottle 21, respectively, inside the cabinet 43 to the Aux. PITC valve 1 pass through heavy walled polypropylene tubes 46 for protection against leaks and breakage.

In operation, the Aux. PITC valve 1 is either in an "on" or "off" position, depending on the control signals received from the control unit 40 described in further detail below. With the valve in the "off" position, the Aux. PITC syringe pump 11 refills with radioactive PITC from the Aux. PITC reagent bottle 21. With the valve in this "off" position, the radioactive PITC is shut off from the rest of the degradation sequencing system. With the valve in the "on" position the syringe pump 11 empties by pumping the radioactive PITC into the main system through the Aux. PITC valve 1.

Figure 2:
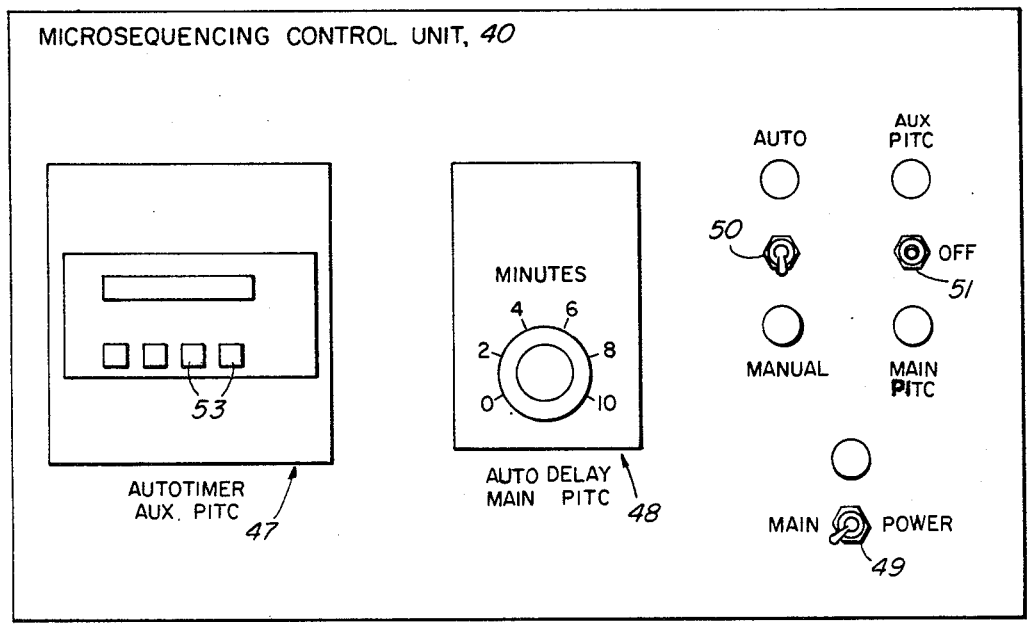
FIG. 2 is a front view of the control unit of the present invention.

The control unit 40 of the microsequencing system of the present invention controls the operation of the radioactive PITC coupling step as an optional auxiliary part of the Edman degradation analysis. As shown in FIGS. 1 and 2, the control unit 40 comprises a programmable timer 47, an adjustable time delay means 48, function switches 49, 50, 51, and a 4-way solenoid valve 62 discussed above.

After the microsequencing system is initiated at the beginning of the PITC step of the main sequencing cycle, the operator can have the microsequencing system perform either automatically according to preprogrammed instructions for repetitive cycles, or he can have the system perform in a manual mode for any or all cycles. This election is accomplished via the function switches 49, 50, 51 on the control unit 40. Referring to FIG. 2, switch 49, labelled "MAIN POWER" in FIG. 2, controls the overall power of the microsequencing control unit. Furthermore, the "MAIN POWER" switch 49 serves as the logic signal to the main sequencer programmer 30. If this switch is "on", then the main sequencer programmer will know that the auxiliary PITC microsequencing system should be introduced before the main, or non-radioactive, PITC step. If, however, the "MAIN POWER" switch 49 is "off", then the main sequencer programmer will know that the auxiliary PITC step will not be performed in that particular cycle. Function switch 50 allows the operator to select automatic ("AUTO") or manual ("MANUAL") operation of the microsequencing system. Under automatic operation the timer 47 and time delay means 48 are pre-set by the operator, and both the duration of the auxiliary radioactive PITC step and the time delay are performed automatically by the microsequencing system for each degradation cycle.

The timer 47 controls the duration of the delivery of the radioactive PITC during automatic operation of the microsequencing system. The timer 47 can be push-button programmed by the operator with 0.1 minute accuracy to deliver a precise volume of radioactive PITC. The duration, in minutes, of automatic radioactive PITC delivery is preselected by the operator by pushing in the buttons 53 to any desirable amount of time. After the main sequencer programmer has determined that there will be a microsequencing operation, as discussed above, the entire microsequencing operation is then controlled by the microsequencing system of the present invention. The radioactive PITC will be delivered by the Aux. PITC pump 11 through Aux. PITC valve 1 to the protein or peptide sample in the reaction column 10 until the automatic timer 47 runs down to zero. At this point, the control unit 40 determines whether the operator has programmed a time delay, before returning to the main sequencer programmer. The timer 47 of the preferred embodiment is manufactured by Automatic Timing & Controls Co. (ATC), Model No. 325A347A10PX. It is to be understood that a more precise timer, with a greater precision, may be used if desired.

The automatic time delay means 48 permits the radioactive PITC coupling reaction step to continue before the non-radioactive PITC is added to the protein or peptide derivative in the column 10. The adjustable time delay means 48 can be programmed to introduce a 0–10 minute delay following the pumping of labelled reagent. The present invention is not, however, limited to the specific duration of the time delay, and a longer time delay can be utilized if desirable. During this time delay the non-radioactive PITC and buffer pumping of the main sequencer is stopped and the radioactive PITC is allowed to stand in the reaction column 10. The time delay means 48 of the preferred embodiment is manufactured by Automatic Timing & Controls Co. (ATC) Model No. 322BO14A12CS, but it is understood that other time delay means obvious to those skilled in the art can be used. It should also be noted that both the timer 47 and time delay means 48 provide fine time accuracy, thereby permitting precise and economical use of the radioactive PITC.

In practice, the microsequencing system of the present invention is used to provide a pulse labelling procedure using radioactive and non-radioactive PITC. The control unit 40 is activated by the main PITC signal of the main sequencer programmer. The timer 47 is used to program the first 2–3 minutes of the PITC pumping for the radioactive reagent. The adjustable time delay means 48 is set for preferably 1–2 minutes so that the radioactive PITC stands in the reaction column 10 to maximize this segment of the coupling reaction. Finally, the remaining minutes of the main sequencer PITC program control the delivery of non-radioactive PITC which drives the coupling reaction to completion. At the end of the main sequencer PITC program, the control unit 40 resets for the next cycle, i.e. the timer 47 and time delay means 48 automatically reset from zero to the values preselected by the operator for the preceding cycle.

The foregoing description of the control unit 40 concerned automatic operation, i.e., function switch 50 being in the "AUTO" position. If, however, the operator wishes to control the microsequencing system manually, the function switch 50 is placed in the "MANUAL" position. Under manual operation the timer 47 and time delay means 48 have no control over delivery of the radioactive PITC. Instead, function switch 51 provides the operator control during manual operation. When the operator wants the auxiliary PITC to begin, switch 51 is placed in the "AUX PITC" position. This auxiliary radioactive PITC step will continue for as long as switch 51 is in this position. When the operator wants this step to end, he places switch 51 in the "OFF" position. As long as switch 51 is in this "OFF" position, the operator is providing a time delay, just as the time delay means 48 did under automatic operation. Then, when the operator wants the main non-radioactive PITC step to begin, switch 51 is placed in the "MAIN PITC" position.

The radioactive PITC preferably used with the microsequencing system of the present invention is $^{35}S$- or $^{14}C$- or $^{3}H$-labelled phenyl isothiocyanate, available from Amersham/Searle Corp. or New England Nuclear.

As mentioned above, the microsequencing system of the present invention forms an auxiliary add-on unit to a main Edman degradation sequencing system. The complete total sequencing system with the microsequencing system of the present invention is shown in FIG. 1. As shown therein, the non-radioactive PITC for the coupling step is contained in the main PITC reagent bottle 22, and is pumped into the main sequencing system by main PITC pump 12 through main PITC valve 2. As discussed previously, the radioactive PITC is contained in the Aux. PITC reagent bottle 21 and pumped by the Aux. PITC pump 11 through Aux. PITC valve 1 into the main sequencing system. The buffer solution is contained in buffer reagent bottle 23, and is pumped into the main sequencing system by buffer pump 13 through buffer valve 3. The washing reagents methanol (MeOH) and dichloroethane (DCE) are contained in MeOH and DCE reagent bottles 24, 25 respectively, and pumped by washing reagent pump 14 through MeOH and DCE valves 4, 5 respectively. The trifluoroacetic acid (TFA) is contained in TFA reagent bottle 26, and pumped by TFA pump 16 through TFA valve 6.

As shown in FIG. 1, the main sequencer is designed for dual-column operation, and a reagent partition valve 7 divides the above reagents, as well as the radioactive PITC, into two portions, one for each reaction column 10. Furthermore, a waste/collection valve 8 is provided to separate the products from the reaction columns 10 into waste and collection portions. The waste portions are collected by waste collector 61. The collected portions are further separated by the collection partition valve 9 before being collected by the fraction collectors 60. These collected portions can then be analyzed by conventional means, such as two dimensional thin layer chromatography and autoradiography.

Having thus described the principles of the invention, together with an illustrative embodiment thereof, it is to be understood that although specific terms are employed they are used in a generic and descriptive sense and not for purposes of limitation, the scope of the invention being set forth in the following claims.

We claim:

1. In a system for the Edman degradation analysis of protein material wherein a main sequencing system includes a reaction vessel, means for separately valving, pumping and piping preselected reagents to said vessel, and a programmable control for said main system for actuating said valving and pumping means according to a preselected order, auxiliary apparatus for pulse labelling a microquantity of said protein material comprising; an isolated container for a coupling reagent to be introduced into the reaction vessel between two steps in the process of the main sequencer, isolated valve, pumping and piping means for conveying said coupling reagent to said reaction vessel, means for deriving an actuating signal for said auxiliary apparatus from the control of the main sequencer, an isolated programmable control for said auxiliary apparatus for controlling the amount of said coupling reagent to be introduced into said vessel, means for actuating said isolated control in response to said actuating signal, means associated with said isolated control for interrupting the operation of said main sequencer while the auxiliary apparatus is active, and controllable time delay means for reactivating said main sequencer after the elapse of a predetermined period of time following the completion of the introduction of the coupling reagent into said vessel; whereby said auxiliary apparatus provides complete isolation of its reagent from the main sequencer permitting the safe use of radioactive labelling materials and efficient use thereof by introducing same separately into said vessel in high concentration at the start of the cycle of said auxiliary apparatus.

2. The apparatus defined in claim 1 further characterized by the auxiliary apparatus being housed as a separate unit, and a 4-way valve connecting same to the main system whereby normal operation of the main system or introduction of the separate reagent may be done in complete isolation and at will.

3. The apparatus defined in claim 1 further characterized by automatically resettable timing means for regulating said isolated programmable control whereby sequencing of the main and auxiliary systems can be done without the need for operator participation.

4. The apparatus defined in claim 1 further characterized by means for controlling the quantity of said coupling reagent pumped to said vessel in any given cycle including a positive action pump and a controllable timer for regulating the duration of the positive stroke of said pump whereby controlling the setting of the timer regulates the amount of reagent pumped.

5. In the Edman process of sequential degradation of protein material wherein the protein material is reacted with a coupling agent, the process steps of
    (1) interrupting the degradation process of a given quantity of said protein material and before the coupling reaction of that given quantity is complete;
    (2) contacting said given quantity of protein material with a quantity of radioactive coupling agent which is insufficient to complete the coupling reaction of the protein material;
    (3) holding the radioactive coupling agent in contact with said protein material for a period predetermined to maximize the coupling reaction therewith, and
    (4) thereafter re-activating the degradation process by contacting said protein material with sufficient non-radioactive coupling agent to drive the coupling reaction to completion.

* * * * *